US010856067B2

United States Patent
Jenkins et al.

(10) Patent No.: US 10,856,067 B2
(45) Date of Patent: *Dec. 1, 2020

(54) DOSIMETRY HEARING PROTECTION DEVICE WITH TIME REMAINING WARNING

(71) Applicant: Honeywell International Inc., Morris Plains, NJ (US)

(72) Inventors: John Jenkins, San Diego, CA (US); Neal Muggleton, Stevenage (GB); Viggo Henriksen, Trondheim (NO); May Wilson, Wokingham (GB); Trym Holter, Trondheim (NO); Claes Haglund, Odakra (SE)

(73) Assignee: Honeywell International Inc., Morris Plains, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/593,790

(22) Filed: Oct. 4, 2019

(65) Prior Publication Data

US 2020/0037060 A1      Jan. 30, 2020

Related U.S. Application Data

(63) Continuation of application No. 16/003,297, filed on Jun. 8, 2018, now Pat. No. 10,440,463.

(Continued)

(51) Int. Cl.
*H04R 1/10* (2006.01)
*G01H 3/12* (2006.01)
(Continued)

(52) U.S. Cl.
CPC ............ *H04R 1/1083* (2013.01); *A61F 11/14* (2013.01); *G01H 3/12* (2013.01); *G08B 21/18* (2013.01); *H04R 1/1008* (2013.01); *H04R 1/1041* (2013.01)

(58) Field of Classification Search
CPC .. H04R 1/1083; H04R 1/1008; H04R 1/1041; G01H 3/12; G01H 3/14; G08B 21/18; A61F 11/14
(Continued)

(56) References Cited

U.S. PATENT DOCUMENTS

| 10,440,463 B2 | 10/2019 | Jenkins et al. |
| 2006/0262938 A1 | 11/2006 | Gauger et al. |

(Continued)

FOREIGN PATENT DOCUMENTS

| WO | 2010/030889 A1 | 3/2010 |
| WO | 2018/148356 A1 | 8/2018 |

OTHER PUBLICATIONS

Non-Final Rejection dated Jan. 11, 2019 for U.S. Appl. No. 16/003,297.
(Continued)

*Primary Examiner* — Vivian C Chin
*Assistant Examiner* — Con P Tran
(74) *Attorney, Agent, or Firm* — Alston & Bird LLP (57) ABSTRACT

A hearing protection device configured to measure the noise exposure of a user and to provide a time remaining estimate until a maximum noise exposure level is achieved. Generally, the hearing protection device may comprise a sound sealing section, a microphone configured to generate a detected sound signal indicative of the measured sound level at the user's ear canal, a memory/storage configured to record the detected sound signal as sound exposure history, a timer configured to measure the amount of time the hearing protection device is exposed to sound, and a processor configured to receive a timer signal from the timer and the detected sound signal to calculate a time remaining estimate until reaching the maximum noise exposure level. Additionally, the maximum noise exposure level may be based on industry regulations or personalized hearing thresholds.

17 Claims, 2 Drawing Sheets

Related U.S. Application Data (60) Provisional application No. 62/517,670, filed on Jun. 9, 2017.

(51) Int. Cl.
*G08B 21/18* (2006.01)
*A61F 11/14* (2006.01)

(58) Field of Classification Search
USPC .......................... 381/56, 58, 59, 72, 122, 91
See application file for complete search history.

(56) References Cited

U.S. PATENT DOCUMENTS

| | | |
|---|---|---|
| 2007/0129828 A1 | 6/2007 | Lee et al. |
| 2007/0186656 A1 | 8/2007 | Goldberg et al. |
| 2008/0137873 A1 | 6/2008 | Goldstein |
| 2008/0159547 A1 | 7/2008 | Schuler et al. |
| 2008/0205660 A1 | 8/2008 | Goldstein |
| 2008/0212787 A1 | 9/2008 | Goldstein et al. |
| 2010/0135502 A1 | 6/2010 | Keady et al. |
| 2012/0321094 A1 | 12/2012 | Schiller et al. |
| 2013/0094658 A1 | 4/2013 | Holter |
| 2013/0101126 A1 | 4/2013 | Van et al. |
| 2014/0192990 A1 | 7/2014 | Cheng |
| 2015/0110278 A1 | 4/2015 | Andersen |
| 2015/0223000 A1 | 8/2015 | Bran et al. |
| 2015/0287421 A1 | 10/2015 | Benway et al. |
| 2015/0379994 A1* | 12/2015 | Goldstein ............... G06F 21/10 704/260 |
| 2016/0165340 A1 | 6/2016 | Benattar |
| 2017/0188166 A1 | 6/2017 | Eberbach et al. |
| 2018/0041847 A1 | 2/2018 | Umicevic |

OTHER PUBLICATIONS

Notice of Allowance and Fees Due (PTOL-85) dated May 29, 2019 for U.S. Appl. No. 16/003,297.
Communication pursuant to Rules 161(1) and 162 dated Sep. 20, 2019, 3 pages.
International Search Report and Written Opinion for Application No. PCT/US2018/017335, dated May 9, 2018, 12 pages.
Non-Final Rejection dated Mar. 19, 2020 for U.S. Appl. No. 16/479,272.
CN Office Action dated Aug. 21, 2020 for CN Application No. 201880010225.
CN Search Report dated Aug. 10, 2020 for CN Application No. 201880010225.
English Translation of CN Office Action dated Aug 21, 2020 for CN Application No. 201880010225.
Notice of Allowance and Fees Due dated Sep. 16, 2020 for U.S. Appl. No. 16/479,272.
Notice of Allowance and Fees Due dated Oct. 15, 2020 for U.S. Appl. No. 16/479,272.

* cited by examiner

DOSIMETRY HEARING PROTECTION DEVICE WITH TIME REMAINING WARNING

CROSS-REFERENCE TO RELATED APPLICATIONS

The present application is a continuation of U.S. patent application Ser. No. 16/003,297 filed Jun. 8, 2018 by John Jenkins, et al. and entitled "Dosimetry Hearing Protection Device with Time Remaining Warning," which claims priority to U.S. Provisional Patent Application Ser. No. 62/517,670 filed Jun. 9, 2017 by John Jenkins, et al. and entitled "Dosimetry Hearing Protection Device (HPD) with Time Remaining Warning," each of which is incorporated herein by reference as if reproduced in its entirety.

STATEMENT REGARDING FEDERALLY SPONSORED RESEARCH OR DEVELOPMENT

Not applicable.

REFERENCE TO A MICROFICHE APPENDIX

Not applicable.

FIELD

The present disclosure relates generally to a method and apparatus for monitoring noise, and more particularly, to a method and apparatus for monitoring noise levels and predicting time of noise exposure remaining with regards to a hearing protection device.

BACKGROUND

In industrial settings, an individual's hearing health is dependent on the amount of noise the individual is exposed to over a certain period of time. Typically, the accumulated amount of noise (e.g. dose in terms of an average noise level) and the maximum level of noise to which an individual is exposed to during the workday are strictly regulated by industry guidelines, such as the Occupational Safety and Health Administration (OSHA) in the United States.

Generally, noise data measurements may include impulse noise which relates to noise occurring for a very short duration (e.g. less than a few thousandths of a second) and continuous noise which relates to noise occurring longer in duration (e.g. extending over seconds, minutes, or hours). An example of regulating the noise data measurements may include an eight-hour time weighted average (TWA) which is the average of all levels of impulse noise and continuous noise to which an individual is exposed to during a typical eight-hour work shift. For example, the OSHA guideline/regulation for an eight-hour TWA is a maximum noise exposure of 90 dBA (decibels measured on the A scale (slow response) are generally less sensitive to very low frequencies and very high frequencies). Additionally, for individuals exposed to noise between 85-90 dBA, OSHA requires employers to initiate a hearing conservation program which includes annual hearing tests. Thus, in some instances, it may be advisable to try to keep workers on eight hour shifts under 85 dBA, to avoid the need for a hearing conservation program. Depending on the number of hours a worker is exposed to noise, the maximum noise exposure may vary. Under OSHA guidelines (which are subject to change and apply only to the United States), the permissible exposure limit (PEL) of a worker exposed to noise for, for example, 4 hours is 95 dBA and 2 hours is 100 dBA. Typically, the PEL may be determined by lookup tables or calculated based on a known exchange rate.

It is important to note that other countries may also have strict guidelines for noise exposure since noise-induced hearing loss has been and is a prevalent issue within sound industry, for example the agricultural, mining, construction, military, manufacturing, oil, and transportation industries. Often times, reducing noise exposure simply by sound-proofing and guarding machinery may not be an effective method. Additionally, sometimes wearing a hearing protection device may not be enough to prevent hearing loss since, for example, the sound-proofing material/attenuation may not provide sufficient blockage of external noise. Generally, conventional methods may focus on remedial measures taken after excessive noise exposure and may not prevent the user from experiencing hearing damage/loss/impairment. Therefore, within industry there may be a need to provide users with real-time/active feedback to ensure compliance with industry regulations/guidelines and to prevent the user from undergoing remedial measures once hearing damage has already occurred. Therefore, disclosed hearing protection device embodiments implement noise dosimetry and provide the user with real-time data (e.g. amount of time remaining before PEL of the user is reached/exceeded) to safeguard the hearing of the user (such as workers, employees, customers, etc.) against harmful and/or prolonged noise exposure.

SUMMARY

In an embodiment, a hearing protection device may comprise a sound sealing section configured to attenuate external noise from reaching a user's ear canal; at least one microphone configured to generate a detected sound signal indicative of measured sound at the user's ear canal; a memory configured to record the detected sound signal as sound exposure history; a timer configured to measure the amount of time the hearing protection device is exposed to sound; a processor configured to receive one or more of a timer signal from the timer, the detected sound signal from the microphone, and the sound exposure history from the memory, and, in response, to calculate a time remaining estimate and generate an output signal to an output device regarding the time remaining estimate; and an output device configured to receive the output signal from the processor and to generate an output notice to the user indicative of the time remaining estimate in response to the output signal from the processor.

In an embodiment, a method of using a hearing protection device to predict the amount of noise exposure time remaining may comprise generating, by a microphone of the hearing protection device, a sound signal indicative of sound exposure for the specific hearing protection device; transmitting, by the microphone, the sound signal to a processor; transmitting, by a timer, a time signal to the processor, wherein the time signal corresponds to the sound signal received by the processor; calculating, by the processor, an instantaneous sound energy exposure based on the received sound signal and time signal; calculating, by the processor, an estimated future sound energy exposure to determine a noise exposure time remaining based on the received sound signal and time signal; and generating, by the processor, an output signal indicative of the time remaining estimate.

BRIEF DESCRIPTION OF THE DRAWINGS

For a more complete understanding of the present disclosure, reference is now made to the following brief descrip

DETAILED DESCRIPTION

It should be understood at the outset that although illustrative implementations of one or more embodiments are illustrated below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

The following brief definition of terms shall apply throughout the application:

The term "comprising" means including but not limited to, and should be interpreted in the manner it is typically used in the patent context;

The phrases "in one embodiment," "according to one embodiment," and the like generally mean that the particular feature, structure, or characteristic following the phrase may be included in at least one embodiment of the present invention, and may be included in more than one embodiment of the present invention (importantly, such phrases do not necessarily refer to the same embodiment);

If the specification describes something as "exemplary" or an "example," it should be understood that refers to a non-exclusive example;

The terms "about" or "approximately" or the like, when used with a number, may mean that specific number, or alternatively, a range in proximity to the specific number, as understood by persons of skill in the art field (for example, +/−10%); and If the specification states a component or feature "may," "can," "could," "should," "would," "preferably," "possibly," "typically," "optionally," "for example," "often," or "might" (or other such language) be included or have a characteristic, that particular component or feature is not required to be included or to have the characteristic. Such component or feature may be optionally included in some embodiments, or it may be excluded.

Disclosed embodiments relate to a method and apparatus for monitoring noise, and more particularly, to a method and apparatus for monitoring noise levels and predicting noise exposure time remaining (also referred to as time remaining estimate) with regards to a hearing protection device. Exemplary hearing protection devices include earmuffs and earplugs. It should also be understood that while reference below may typically be to a hearing protection device as including dosimetry equipment (such as a microphone), in some embodiments, the dosimetry equipment could be separate and apart from the sound sealing section of the hearing protection device (in which case, a transceiver may allow for communication there between). Generally, the hearing protection device may predict the amount of noise exposure time remaining by implementing a microphone configured to measure detected noise levels at the user's ear canal and generating a detected sound signal indicative of the detected noise levels. Alternatively, an external microphone could be used, with the exposure signal being adjusted to account for the presence of the hearing protection device (reducing the sound exposure on the user's ear). Additionally, an exemplary embodiment may comprise a timer configured to measure the amount of time the hearing protection device is exposed to sound, a memory/storage configured to record the detected sound signal as sound exposure history, and/or a processor configured to receive (as input) a timer signal from the timer (or in other embodiments the processor may compute the time using detected sound signal/sound exposure history) and the detected sound signal from the microphone and/or the sound exposure history from the memory/storage. Generally, the processor may then compute a time remaining estimate (based on the inputs) and generate an output signal which may be transmitted to an output device (for alerting the user, for example, regarding the approaching PEL. Typically, the output device may receive the output signal from the processor and generate an output notice to the user indicative of the time remaining estimate. The output device may comprise a handheld/portable device (e.g. smart phone, tablet, etc.), and/or a user interface located on the hearing protection device (such as a speaker configured to detect sound into the user's ear canal).

In some embodiments, the microphone may be configured to receive acoustic signals indicative of the external noise environment and the noise transmitted by, for example, any speakers located within the ear cup of the hearing protection device (for example, speakers associated with a communication system or entertainment system). Generally, the microphone may be located close to the user's ear canal, for example near/behind the sound sealing section of the hearing protection device such that the microphone is not blocked or restricted (by, for example, the user's head and/or the sound sealing section). In some embodiments, the microphone may be located in or on the sides of both ear cups of the hearing protection device (to account for differences in noise exposure between the left ear and the right ear and/or to separately configure the noise exposure limits for the left ear and the right ear). In some cases, the sound signals received by the microphone in the left ear may be averaged with the sound signals received by the microphone in the right ear to provide an overall user sound exposure. In some embodiments, the microphone may be located in only one ear cup of the hearing protection device with that signal sensing as an estimate for both ears.

In some embodiments, there may be an additional microphone (for example, associated with any ear being measured). In such instances, one microphone may typically be placed on the exterior of the hearing protection device, and the other microphone may typically be placed on the interior of the hearing protection device as previously described. Generally, the microphone located on the exterior may detect sound signals from the external/surrounding environment. The sound signals detected from the external/surrounding environment by the external microphone may serve to form a noise map in some embodiments. In some instances, the external sound signals from various hearing protection devices may be compiled, and may allow for a more accurate prediction of time remaining (by tracking the user's location within the field and comparing that with the (average) noise level of that area). The external microphone signal and/or noise map may also be used as a device check, for example to determine if there is any modification.

In some instances, disclosed embodiments may be configured for shared use (e.g. for use by more than one user, e.g. sequentially/serially). Typically, for shared use, the hearing protection device may be reset (e.g. via a button located on the hearing protection device, via the output device, via determination that there has been a change of user, etc.) each time a new user uses the hearing protection device (although in some cases, the hearing protection device may not be reset). The hearing protection device may be able to determine who is wearing/using the hearing protection device at a specific time, perhaps through built-in ear scanning or voice recognition. In some embodiments, the hearing protection device may determine who the user is by a pairing sequence, for example with a Near Field Communication (NFC) ID card or a smart phone (registered to the user) or by scanning an ID card (for example, with a magnetic strip or other identifier). Generally, the data gathered by the hearing protection device may be tagged with user information along with the time/counter in some embodiments. Thus, the data may be extracted such that all data pertaining to that specific user may be compiled together by, for example, a software application. In this manner, a reset may not need to occur and various parts of the stored data tagged with an individual's information may be pieced together to provide the specific sound exposure history and to allow for the device to determine time remaining estimate and notify the user (for example, as PEL approaches).

In other instances, disclosed embodiments may be configured for private use (e.g. hearing protection device is not shared, but is for use with one specific user). Typically, for private use, the hearing protection device may be reset when issued to the user. Additionally, a sliding window principle may be implemented. US20130094658A1 by Trym Holter and entitled "Sound Exposure Monitor for Hearing Protection Device" describes the sliding window principle and is hereby incorporated by reference for all purposes as if reproduced in its entirety to the extent that it is compatible (e.g. not inconsistent) with and/or does not directly contradict disclosure herein (e.g. the explicit disclosure herein would always govern/trump in instances of contradiction, inconsistency, or incompatibility).

Typically, the sliding window method may allow the hearing protection device to track sound exposure without reset for an unlimited period of time. More typically, however, for example, the sliding window may be set to last a pre-determined duration of the longest shift that the worker may work (e.g. eight hour time period). In such instances, the past eight hours (or however long the sliding window is pre-set for) of sound exposure could be used when calculating (via the time remaining) the cumulative sound exposure (e.g. by subtracting the sound exposure calculated prior to the sliding window of time from the cumulative sound exposure). In this way, the sliding window would essentially automatically reset the device (since it could include quiet time while the device is not in industrial use), and the hearing protection device may not need to be configured for different work patterns (e.g. day shift, night shift, etc.). Generally, a longer sliding window may lead to a more conservative sound exposure estimate.

In some embodiments, the sliding window may operate by adding a recent short duration of sound exposure and subtracting the short duration of sound exposure from a pre-determined amount of time ago (e.g. if the sliding window is set to 8 hours, the short duration of sound exposure from 8 hours ago would be subtracted and the recent short duration of sound exposure would be added). The short duration of sound exposure may vary between 10 seconds to approximately 2 minutes. Thus, if the short duration of sound exposure is set to 10 seconds, the device may update the cumulative sound exposure every 10 seconds by adding the amount of sound exposure in the past 10 seconds and subtracting the amount of sound exposure in the first 10 seconds of the sliding window. In this manner, the device may keep track of the updated cumulative sound exposure to notify the user of the current cumulative sound exposure.

In some embodiments, the device might record sound exposure even when off/resting/not in use. In other instances, the device might simply track time when off/resting/not in use (e.g. powered down) and apply an assumed safe sound exposure level (e.g. less than 80 dBA) for that period. So, for example, the device may have a timer that always remains on, or when the device is shut down, the device might start the time (e.g. time and date stamp); and then when the device is powered up, it might retrieve (via interaction with a smart phone/internet/atomic clock, etc.) the current time (e.g. time and date stamp) and determine the length of the down-time. Thus, when determining the exposure time remaining, cumulative noise exposure, etc. the processor of the hearing protection device may only take into account the sliding window time exposure, for example, the past eight hours or four hours and calculate forward the amount of time remaining based on the estimated/current sound exposure. In some embodiments, the hearing protection device may be configured to take into account the past 2 hours, 3 hours, 5 hours, 6 hours, 8 hours, etc. In some embodiments, the hearing protection device may be configured to have a pre-set time period (e.g. to fit into the normal 9-5 work schedule). Thus, the hearing protection device may be configured to reset prior to the start of the work shift, and may begin detecting the noise exposure levels once the work shift begins. In some embodiments, the hearing protection device may detect a period of inactivity (e.g. a time period longer than 2 hours, 4 hours, 6 hours, 8 hours, etc.).

In some embodiments, the hearing protection device may comprise a motion sensor allowing it to determine when the hearing protection device is in use and/or when it is not in use. In other words, after a period of inactivity (e.g. no movement), the hearing protection device may reset automatically. The period of time required for reset due to inactivity may vary (e.g. 1 hour, 2 hours, 4 hours, etc.). In some embodiments, reset might be based on a pre-determined period of inactivity (e.g. as determined by motion sensor) in combination with a sound measurement below a pre-set threshold. In some embodiments, the hearing protection device may not necessarily reset (e.g. set the accumulated noise level to 0 dBA). The hearing protection device may temporarily pause detection of sound/noise exposure when it detects inactivity (e.g. for a period longer than 3 minutes, 4 minutes, 5 minutes, etc.), and it may continue/un-pause detection of sound/noise exposure once it detects activity (e.g. movement sensed by the motion sensor).

Generally, the disclosed embodiments may be configured to calculate (e.g. via processor) a real-time noise exposure level (e.g. cumulated sound energy exposure, current/instantaneous sound energy exposure). The disclosed embodiment may use the sound exposure history, along with the running time (e.g. from the timer), to determine current/instantaneous sound energy exposure. Typically, the processor may also perform calculations (e.g. integration) to determine the cumulated sound energy exposure. Generally, the processor may implement lookup tables and/or a pre-determined/pre-defined algorithm to calculate the current/instantaneous sound energy exposure. In some embodiments, the memory/storage may store the current/instantaneous sound energy exposure along with the time to serve as the sound exposure history.

In some embodiments, the sound exposure history may be used to calculate (e.g. by the processor) the time remaining estimate. Generally, the time remaining estimate may be based on the current/instantaneous sound energy exposure, industry standards (e.g. OSHA), and the estimated expected/future sound energy exposure. Typically, the estimated/expected future sound energy exposure may be determined by extrapolation (e.g. linear regression, non-linear regression, other regression model, etc.). In this manner, the time remaining estimate may be determined by adding the estimated/expected future sound energy exposure with the sound exposure history (for a pre-determined amount of time surpassed since the user began using the hearing protection device). For example, the estimated/expected future sound energy exposure may be determined by extrapolating based on the sound energy exposure gathered in the past, for example, most recent 15 minute window (although the window may vary/range from a few seconds to a few hours, in different embodiments; with some embodiments, using the most recent 1 min., 5 min., 10 min. window). So for example, an average level of noise during the window could be used to determine the extrapolation, perhaps using a window of LAeqXmins where X is the length of the window (e.g. 5, 10, or 15 minutes). And in some embodiments, the rate of change could factor into the extrapolation by using one or more windows of such blocks of time to predict the rate of change going forward. In some cases, for example when the sound exposure history does not contain enough sound energy exposure data, the processor may calculate the time remaining estimate based on the current internal noise level/current sound energy exposure.

Typically, the estimated/expected future sound energy exposure may be determined using the sound exposure history. In some embodiments, the estimated/expected future sound energy exposure may be determined by projecting forward the maximum amplitude from the sound exposure history (for example, within the most recent window). In some embodiments, the estimated/expected future sound energy exposure may be determined by projecting forward the average amplitude (for example, of the most recent window). In some embodiments, the estimated/expected future sound energy exposure may be determined by projecting forward the estimated trend of change (for example, the average rate of change of the most recent window being used to project forward).

In some embodiments, the future sound energy exposure may be determined based on some combination of the above techniques. For example, either the maximum or the average from the sound exposure window could be used with the rate of change information to project future sound energy exposure. And in some instances, a shorter window (such as 5, 10, or 15 minutes) might be used for the average or maximum determination, while a larger window (for example, the entirety of the sliding window or data since reset) might be used for the rate of change. So for example, knowing the historical level of sound exposure and the projected rate of change, the processor may calculate the headroom to the maximum safe exposure level (either based on regulating level or some other pre-set level) providing an estimate of time remaining at that particular time. The estimate would be dynamic, and would adjust as sound exposure history is updated (e.g. each specific time could have a different projection as the input data changes/updates).

In some cases, a personalized maximum sound energy exposure may be determined for users with previous hearing damage/loss. For example, the industry maximum sound energy exposure may be 85 dbA, but the user's personalized maximum sound energy may be lower (e.g. 80 dBA) because he/she already has a pre-existing degree of hearing damage/loss. In this case, an instantaneous fit test may be incorporated within the hearing protection device to allow the user to determine his/her own personalized maximum sound energy exposure. Or, the personalized maximum sound energy exposure may be stored within memory (for example, based on prior hearing testing), and, in some embodiments, may be tagged with the user's identification (e.g. name, ID number, etc.). The processor may then perform calculations to determine the amount of time remaining based on the personalized maximum sound energy exposure, for example stored within memory.

The processor may continually update the time remaining estimate based on the current/instantaneous sound energy exposure. In some embodiments, the processor may update the time remaining estimate in response to a detected sound signal amplitude/volume increase or decrease (for example, of more than a pre-determined amount). In some embodiments, the processor may periodically (e.g. every 10 min, 15 min, 30 min, etc.) update the time remaining estimate. The rate at which the processor updates the time remaining estimate may depend on the rate of power consumption of the hearing protection device and/or user preference. Additionally, the rate at which the processor performs calculations may vary. In some embodiments, the processor may be configured to continuously evaluate the time remaining estimate (but perhaps only report to the user periodically). In some embodiments, the processor may evaluate the time remaining estimate periodically (e.g. 5 min, 10 min, 15 min, etc.). In some embodiments, the processor may evaluate the time remaining estimate based on user inquiry/input to, for example, a user interface and/or the output device. One or more trigger event may cause the processor to calculate an updated time remaining (e.g. time remaining calculated based on any combination of triggers/intervals).

Typically, once the processor updates the time remaining estimate (or alternating periodically and/or at certain trigger events, in the case of continuous calculations), the processor may generate an output signal indicative of the time remaining estimate. In some embodiments, the output signal may be transmitted to an output device configured to transmit an output signal to the user when the time remaining estimate changes by a certain amount (e.g. 1%, 2%, 5%, 10%, etc.).

In some embodiments, the time remaining estimate may change too frequently and may serve as an annoyance to some users. Thus, the time remaining estimate may be transmitted via the output device to the user in response to an inquiry from the user (e.g. signal from a user interface). In some embodiments, the time remaining estimate may be transmitted to the output device periodically (e.g. 5 min, 10 min, 15 min, etc.). In some embodiments, the time remaining estimate may be transmitted to the output device if the time remaining estimate has changed by a pre-determined/pre-set amount (e.g. 5 min, 10 min, 15 min, 30 min, 1 hour, etc.). In some embodiments, the time remaining estimate may be transmitted when the time remaining reaches a pre-determined threshold (e.g. only 1 hour left). In some embodiments, the hearing protection device may be integrated with a task/planning system so that the hearing protection device may obtain data/information about when the work is due to complete and then transmit a time remaining estimate/warning when the time remaining estimate is less than the job task in operation (for example, the end of the work shift). In some embodiments, the time remaining estimate may be transmitted to the user if/when the user enters/exits a known noisy area (e.g. determined by a noise map). Typically, this may occur once the user walks through a doorway or is in proximity to workers or by geolocation (e.g. connected with some external location system). In some embodiments, the time remaining estimate may be transmitted to the output device in any combination of ways described.

In some embodiments, the device could record sound exposure (and time) even if the hearing protection device is not worn in protective position (for example, even if the hearing protection device earmuff is worn around user's neck), since this could still be indicative of exposure to user.

In some embodiments, the processor could be located within the housing of the hearing protection device or physically connected (e.g. by wire) to the hearing protection device. In other embodiments, the processor could be separate and apart from the hearing protection device and might merely be communicatively coupled to the hearing protection device. For example, the processor could be a smart phone carried by the user or a central computer for a facility or cloud computing. For a remote (e.g. separate and apart) processor, the hearing protection device would typically also comprise a transmitter/transceiver (such as a wireless transceiver) to allow the processor to transmit and/or receive the inputs and/or outputs as described above (such as measured sound and/or sound output signals (e.g. indicative of time remaining) to the user).

Typically, the timer may be configured to measure the amount of time the hearing protection device is exposed to sound and/or is worn by the user. In some embodiments, the timer may continuously transmit timer signals to the processor (e.g. with no beginning or end defined). In some embodiments, the timer may begin and end transmission of timer signals based on when the reset mechanism is triggered. In some embodiments, the timer may be configured to interact with a sensor (e.g. motion sensor, pressure sensor, etc.) to detect when the user is wearing the hearing protection device. While persons of skill should understand the disclosed embodiments based on the above disclosure, the following figures may provide specific examples that may further clarify the disclosure.

Figure 1:
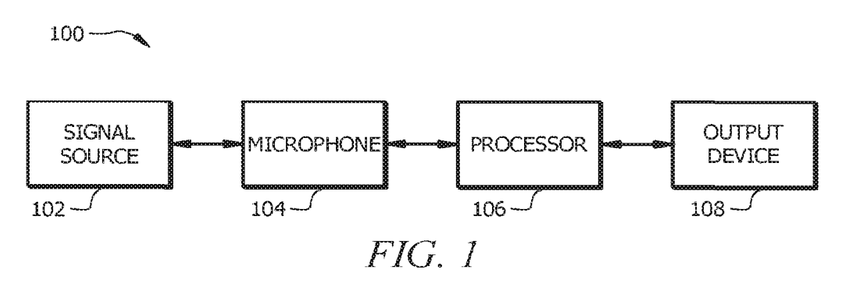
- FIG. 1 is a simple block diagram of an exemplary system of a dosimetry hearing protection device configured to predict a noise exposure time remaining.

FIG. 1 illustrates a general block diagram of an embodiment of a hearing protection device 100 configured to determine a current/instantaneous sound energy exposure, cumulative sound energy exposure, and/or a time remaining estimate (of noise exposure until a pre-determined/pre-set threshold is reached). Typically, the hearing protection device 100 may comprise a signal source 102 (also referred to as detected sound signal), at least one microphone 104, a processor 106, and an output device 108. Generally, the signal source 102 may be representative of the noise generated in the surrounding environment and/or it may arise from the noise generated by the speakers of the hearing protection device 100. The signal source 102 may then be detected by the one or more microphones 104. In some embodiments, at least one microphone 104 may be located within the ear cup of the hearing protection device 100 (near the interface between the user's head and the sound sealing section or as close to the user's ear canal as possible). In some embodiments, a second microphone 104 may be located on the exterior of the ear cup of the hearing protection device 100. Typically, such a second microphone 104 may be configured to detect the noise generated in the surrounding environment (prior to attenuation by the hearing protection device 100). In some embodiments, this may allow for compilation of noise data from several hearing protection devices to form an accurate noise map. The noise map may serve as a guide to predicting the expected/future sound energy exposure of a certain user.

Typically, the one or more microphones 104 may transmit the detected sound signals to the processor 106, and the processor 106 may calculate a time remaining estimate and generate an output signal to an output device 108 regarding the time remaining estimate. In some embodiments, the processor 106 may further comprise a timer and/or a memory/storage. Generally, the timer may transmit timer signals to the processor (upon detection and/or transmission of sound signals by the one or more microphones 104). Generally, the memory/storage may be configured to store the sound exposure history. In other words, the memory/storage may store the detected sound signals along with the corresponding time to the memory/storage. The rate at which data is stored within the memory may vary. In some embodiments, the data may be stored every few seconds (e.g. 5 seconds, 10 seconds, 30 seconds, etc.) or every few minutes (e.g. 1 min, 2 min, 3 min, 5 min, 10 min, 15 min, 30 min, etc.). In some embodiments, the processor 106 may be able to determine the time without a separate timer, for example using the sound exposure history. In some embodiments, the timer and/or the memory/storage may be separate components configured to interact with the processor 106 rather than form a part of the processor assembly. In the exemplary block diagram shown in FIG. 1, the output device 108 may comprise a handheld/portable device (e.g. smart phone, tablet, etc.), the speakers of the hearing protection device 100 (e.g. to provide a voice notification to the user), and/or a user interface located on the hearing protection device 100.

Figure 2:
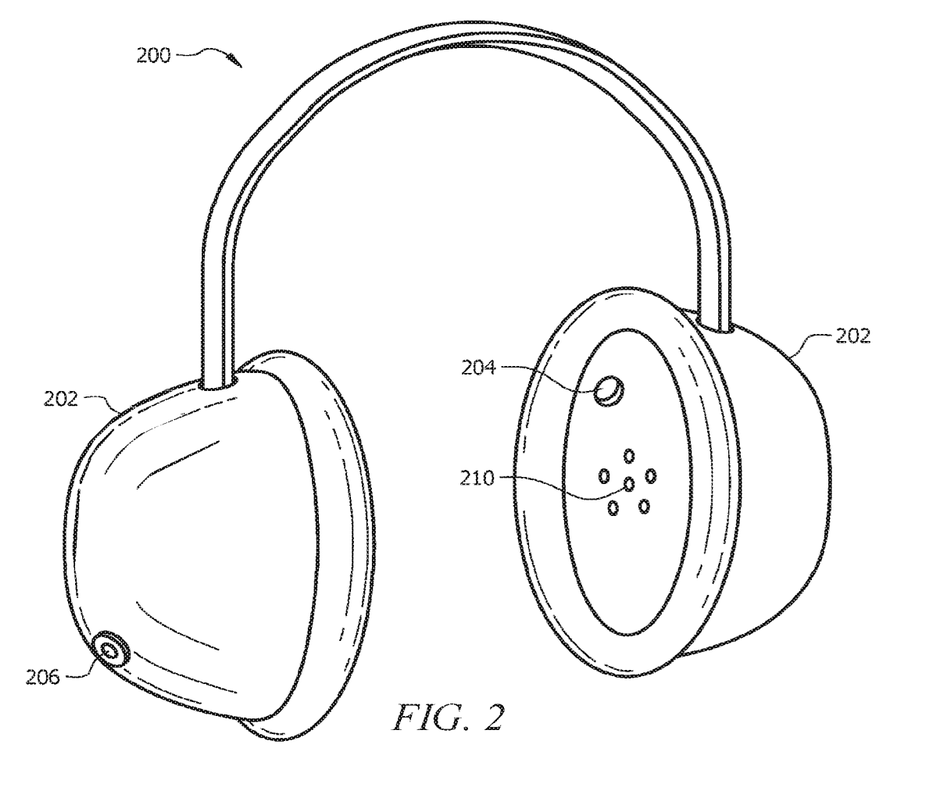
FIG. 2 illustrates a perspective view of an exemplary dosimetry hearing protection device configured to predict the noise exposure time remaining.

FIG. 2 illustrates a perspective view of an exemplary dosimetry hearing protection device 200 configured to predict the noise exposure time remaining. In the exemplary embodiment of FIG. 2, there is a first microphone 204 located near the speakers 210 of the hearing protection device 200. Typically, the first microphone 204 may be configured to detect sound transmitted by the speakers 210 and the noise from the surrounding environment (after the noise passes through the attenuating material of the hearing protection device 200). In this manner, the first microphone 204 may detect sound signals which may enter the user's ear canal. Generally, each ear cup 202 of the hearing protection device 200 may comprise a first microphone 204. In some embodiments, as in the embodiment of FIG. 2, there may be a second microphone 206 located near the external side of the ear cup 202 of the hearing protection device 200. Typically, the second microphone 206 may be configured to detect the noise generated in the surrounding environment (prior to attenuation by the hearing protection device 200). In some embodiments, this may allow for compilation of noise data from several hearing protection devices to form an accurate noise map. The noise map may serve as a guide to predicting the expected/future sound energy exposure of a certain user.

Figure 3A:
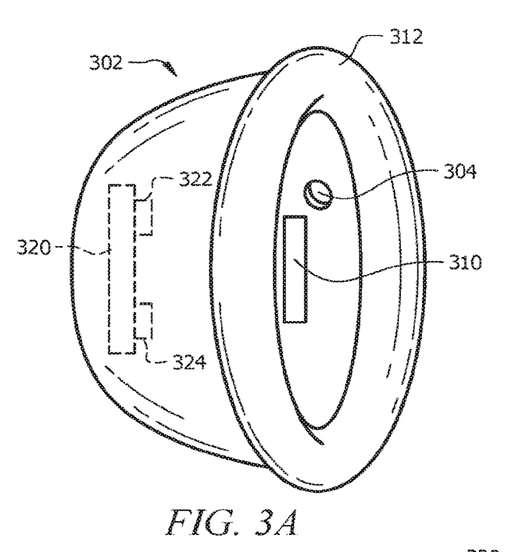
FIG. 3A illustrates a cross-sectional view of an exemplary ear cup of a dosimetry hearing protection device comprising one microphone, a sound sealing section, a processor, a memory/storage, and a timer.

FIG. 3A illustrates a side view of an exemplary ear cup 302 of a dosimetry hearing protection device comprising one microphone 304, a sound sealing section 312, a processor 320, a memory/storage 322, and a timer 324. In the exemplary embodiment shown in FIG. 3A, the microphone 304 may be located on the inner side of the ear cup 302 such that it may receive sound signals from the speaker 310 and the attenuated sound signals from the surrounding environment. Typically, the microphone 304 may transmit the detected sound signals to the processor 320, and the processor 320 may calculate a time remaining estimate and generate an output signal to an output device regarding the time remaining estimate. In some embodiments, the processor 320 may continually update the time remaining estimate based on the current/instantaneous sound energy exposure. In some embodiments, the processor 320 may update the time remaining estimate in response to a detected sound signal amplitude/volume increase or decrease. In some embodiments, the processor 320 may periodically (e.g. every 10 min, 15 min, 30 min, etc.) update the time remaining estimate. The rate at which the processor 320 updates the time remaining estimate may depend on the rate of power consumption of the hearing protection device and/or user preference. Additionally, the rate at which the processor 320 performs calculations may vary. In some embodiments, the processor 320 may be configured to continuously evaluate the time remaining estimate. In some embodiments, the processor 320 may evaluate the time remaining estimate periodically (e.g. 5 min, 10 min, 15 min, etc.). In some embodiments, the processor 320 may evaluate the time remaining estimate based on user inquiry/input to, for example, a user interface and/or the output device.

In the exemplary embodiment of FIG. 3A, the timer 324 may transmit timer signals to the processor 320 (upon detection and/or transmission of sound signals by the one or more microphones 304). Generally, the memory/storage 322 may be configured to store the sound exposure history. In other words, the memory/storage 322 may store the detected sound signals along with the corresponding time to the memory/storage. The rate at which data is stored within the memory/storage 322 may vary. In some embodiments, the data may be stored every few seconds (e.g. 5 seconds, 10 seconds, 30 seconds, etc.) or every few minutes (e.g. 1 min, 2 min, 3 min, 5 min, 10 min, 15 min, 30 min, etc.).

Figure 3B:
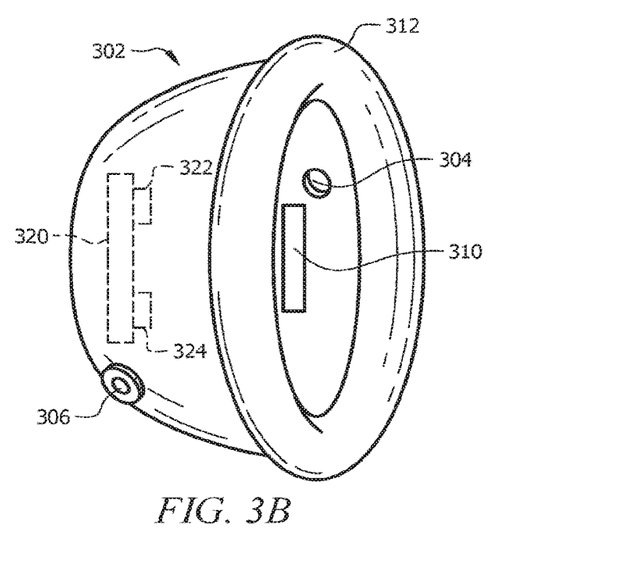
FIG. 3B illustrates a cross-sectional view of an exemplary ear cup of a dosimetry hearing protection device (similar to the exemplary ear cup of FIG. 3A) comprising two microphones, a sound sealing section, a processor, a memory/storage, and a timer.

FIG. 3B illustrates a cross-sectional view of an exemplary ear cup 302 of a dosimetry hearing protection device (similar to the exemplary ear cup of FIG. 3A) comprising two microphones 304 and 306, a sound sealing section 312, a processor 320, a memory/storage 322, and a timer 324. In the exemplary embodiment of FIG. 3B, the components of the hearing protection device (and/or ear cup 302) may be similar to the components of the exemplary hearing protection device (and/or ear cup 302) described in reference to FIG. 3A. However, in the exemplary embodiment of FIG. 3B, there is a second microphone 306 located on the exterior of the ear cup 302. Generally, the second microphone 306 may be configured to detect the noise generated in the surrounding environment (prior to attenuation by the hearing protection device). In some embodiments, this may allow for compilation of noise data from several hearing protection devices to form an accurate noise map. The noise map may serve as a guide to predicting the expected/future sound energy exposure of a certain user. In some embodiments, the time remaining estimate may be transmitted to the user if/when the user enters/exits a known noisy area (e.g. determined by a noise map). Typically, this may occur once the user walks through a doorway or is in proximity to workers or by geolocation (e.g. connected with some external location system).

Having described various devices and methods herein, exemplary embodiments or aspects can include, but are not limited to:

In a first embodiment, a hearing protection device may comprise a sound sealing section configured to attenuate external noise from reaching a user's ear canal; at least one microphone configured (or located) to generate a detected sound signal indicative of measured sound at the user's ear canal (e.g. under the sound sealing section); a memory (or storage) configured to record the detected sound signal as sound exposure history; a timer configured to measure the amount of time the hearing protection device is exposed to sound (over a certain level) and/or is worn by the user; a processor (configured to receive one or more of a timer signal from the timer, the detected sound signal from the microphone, and/or the sound exposure history from the memory/storage, and, in response, to calculate a time remaining estimate and generate an output signal to an output device regarding the time remaining estimate); and an output device configured to receive the output signal from the processor and to generate an output notice to the user indicative of the time remaining estimate in response to the output signal from the processor.

A second embodiment can include the hearing protection device of the first embodiment, wherein the detected sound signals generated by the microphone are indicative of the sound generated by one or more speakers located within the hearing protection device and sound from an external, surrounding environment.

A third embodiment can include the hearing protection device of the first or second embodiment, wherein the processor is configured to generate an output signal to the output device regarding the current/instantaneous sound energy exposure.

A fourth embodiment can include the hearing protection device of the third embodiment, wherein the current/instantaneous sound energy exposure is calculated using data from one or more lookup tables or a pre-determined/pre-defined algorithm.

A fifth embodiment can include the hearing protection device of any of the first through fourth embodiments, wherein the time remaining estimate is calculated based on the current/instantaneous sound energy exposure, industry standards (e.g. OSHA), and the estimated expected/future sound energy exposure.

A sixth embodiment can include the hearing protection device of the fifth embodiment, wherein the estimated expected/future sound energy exposure is determined by pre-existing/pre-stored sound exposure history.

A seventh embodiment can include the hearing protection device of the fifth or sixth embodiment, wherein the estimated expected/future sound energy exposure is determined by extrapolation.

An eighth embodiment can include the hearing protection device of any of the first through seventh embodiments, wherein the processor continually updates the time remaining estimate.

A ninth embodiment can include the hearing protection device of any of the first through eighth embodiments, wherein the processor updates the time remaining estimate in response to a detected sound signal amplitude/volume increase or decrease.

A tenth embodiment can include the hearing protection device of any of the first through ninth embodiments, wherein the processor periodically updates the time remaining estimate at one or more time intervals including every 10 min, 15 min, and/or 30 min.

An eleventh embodiment can include the hearing protection device of any of the first through tenth embodiments, wherein the processor generates an output signal indicative of the time remaining estimate in response to a detected sound signal amplitude increase or decrease.

A twelfth embodiment can include the hearing protection device of any of the first through eleventh embodiments, wherein the processor generates an output signal indicative of the time remaining estimate in response to an inquiry from the user (e.g. signal from a user interface).

A thirteenth embodiment can include the hearing protection device of any of the first through twelfth embodiments, further comprising a reset mechanism, wherein the reset mechanism is configured to receive input from the user, and wherein the reset mechanism is configured to interact with the timer.

A fourteenth embodiment can include the hearing protection device of the thirteenth embodiment, wherein the reset mechanism is configured to reset at the beginning of each work period (day/shift).

A fifteenth embodiment can include the hearing protection device of any of the first through fourteenth embodiments, wherein when the processor generates an output signal indicative of the time remaining estimate, the processor (simultaneously) transmits an alert signal to the speaker, and the speaker generates an alarm (configured to provide a notification to the user) upon receiving an alert signal.

A sixteenth embodiment can include the hearing protection device of any of the first through fifteenth embodiments, wherein a noise map is generated using the sound exposure data collected from various hearing protection devices (e.g. using a second microphone located on the exterior of the hearing protection device.

In a seventeenth embodiment, a method of using a hearing protection device to predict the amount of noise exposure time remaining (before reaching a threshold) may comprise receiving, by a microphone, an acoustic signal indicative of an external noise environment and/or a noise generated by a speaker; generating, by a microphone of the hearing protection device, a sound signal indicative of sound exposure for the specific hearing protection device (e.g., an external noise environment and/or a noise generated by a speaker); transmitting, by the microphone, the sound signal to a processor; transmitting, by a timer, a time signal to the processor, wherein the time signal corresponds to the sound signal received by the processor; storing, by a memory/storage, the sound signal and the time signal; calculating, by the processor, a current/instantaneous sound energy exposure based on the received sound signal and/or time signal; calculating, by the processor, an estimated expected/future sound energy exposure to determine a noise exposure time remaining based on the received sound signal and/or time signal; and generating, by the processor, an output signal indicative of the time remaining estimate.

An eighteenth embodiment can include the method of the seventeenth embodiment, wherein the current/instantaneous sound energy exposure is calculated based on data from look up tables or pre-defined/pre-determined algorithms.

A nineteenth embodiment can include the method of the seventeenth or eighteenth embodiment, wherein the estimated expected/future sound energy exposure is computed by extrapolation or pre-defined sound exposure history.

A twentieth embodiment can include the method of any of the seventeenth through nineteenth embodiments, wherein the microphone is located within an ear cup of the hearing protection device near the user's ear canal.

A twenty-first embodiment can include the method of any of the seventeenth through twentieth embodiments, wherein the output signal indicative of the time remaining estimate is transmitted to an output device.

A twenty-second embodiment can include the method of the twenty-first embodiment, wherein upon transmission of the output signal, the speaker is configured to generate an alarm to alert the user of an update in the time remaining estimate.

A twenty-third embodiment can include the method of any of the seventeenth through twenty-second embodiments, wherein the hearing protection device further comprises a second microphone located at the exterior of the hearing protection device, and wherein the second microphone is configured to detect external/surrounding noise and transmit external/surrounding noise signals to the processor.

A twenty-fourth embodiment can include the method of the twenty-third embodiment, further comprising generating a noise map, wherein the noise map comprises external/surrounding noise signal data compiled from various hearing protection devices.

A twenty-fifth embodiment can include the method of any of the seventeenth through twenty-fourth embodiments, wherein the output device is configured to receive user input (via button, microphone (e.g. voice recognition), etc.).

While various embodiments in accordance with the principles disclosed herein have been shown and described above, modifications thereof may be made by one skilled in the art without departing from the spirit and the teachings of the disclosure. The embodiments described herein are representative only and are not intended to be limiting. Many variations, combinations, and modifications are possible and are within the scope of the disclosure. Alternative embodiments that result from combining, integrating, and/or omitting features of the embodiment(s) are also within the scope of the disclosure. Accordingly, the scope of protection is not limited by the description set out above, but is defined by the claims which follow, that scope including all equivalents of the subject matter of the claims. Each and every claim is incorporated as further disclosure into the specification, and the claims are embodiment(s) of the present invention(s). Furthermore, any advantages and features described above may relate to specific embodiments, but shall not limit the application of such issued claims to processes and structures accomplishing any or all of the above advantages or having any or all of the above features.

Additionally, the section headings used herein are provided for consistency with the suggestions under 37 C.F.R. 1.77 or to otherwise provide organizational cues. These headings shall not limit or characterize the invention(s) set out in any claims that may issue from this disclosure. Specifically and by way of example, although the headings might refer to a "Field," the claims should not be limited by the language chosen under this heading to describe the so-called field. Further, a description of a technology in the "Background" is not to be construed as an admission that certain technology is prior art to any invention(s) in this disclosure. Neither is the "Summary" to be considered as a limiting characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of the claims shall be considered on their own merits in light of this disclosure, but should not be constrained by the headings set forth herein.

Use of broader terms such as "comprises," "includes," and "having" should be understood to provide support for narrower terms such as "consisting of," "consisting essentially of," and "comprised substantially of." Use of the terms "optionally," "may," "might," "possibly," and the like with respect to any element of an embodiment means that the element is not required, or alternatively, the element is required, both alternatives being within the scope of the embodiment(s). Also, references to examples are merely provided for illustrative purposes, and are not intended to be exclusive.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system, or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. A hearing protection device comprising:
   a processor configured to:
   receive, at least, a timer signal, a sound signal indicative of a sound measured by a microphone positioned proximate to a user's ear canal, and a sound exposure history; and
   generate an output signal corresponding to a time remaining estimate indicative of time remaining to achieve a threshold exposure level, wherein the time remaining estimate is calculated based on the received timer signal, the received sound signal, and the sound exposure history.

2. The hearing protection device of claim 1, further comprising an output device configured to generate an output notice to the user indicative of the time remaining estimate, in response to the processor generating the output signal.

3. The hearing protection device of claim 1, wherein the microphone is configured to detect one or more sound signals indicative of at least one of: sound generated by one or more speakers associated with the hearing protection device and sound from an external surrounding environment.

4. The hearing protection device of claim 1, wherein the processor is configured to generate the output signal regarding an instantaneous sound energy exposure.

5. The hearing protection device of claim 4, wherein the instantaneous sound energy exposure is calculated using data from one or more lookup tables or a pre-determined algorithm.

6. The hearing protection device of claim 1, wherein the processor is further configured to calculate the time remaining estimate on an instantaneous sound energy exposure, industry standards, and an estimated future sound energy exposure.

7. The hearing protection device of claim 6, wherein the estimated future sound energy exposure is calculated by using pre-existing sound exposure history.

8. The hearing protection device of claim 7, wherein the processor is further configured to determine the estimated future sound energy exposure by extrapolation.

9. The hearing protection device of claim 1, wherein the processor is configured to update the time remaining estimate based on one of an increase or decrease in an amplitude of the sound signal.

10. The hearing protection device of claim 9, wherein the processor is further configured to generate another output signal indicative of the updated time remaining estimate.

11. The hearing protection device of claim 1, wherein the processor is configured to generate the output signal indicative of the time remaining estimate in response to an inquiry from the user.

12. The hearing protection device of claim 1, further comprising a reset instrument configured to receive input from the user, wherein the reset instrument is configured to interact with a timer.

13. The hearing protection device of claim 12, wherein the reset instrument is configured to reset the hearing protection device at a beginning of a work period of the user.

14. A method of using a hearing protection device to predict a noise exposure time remaining, the method comprising:
   generating a sound signal indicative of a sound exposure to the hearing protection device;
   calculating, by a processor, an instantaneous sound energy based on a received sound signal and a time signal, wherein the instantaneous sound energy is indicative of a current noise exposure;
   calculating, by the processor, an estimated future sound energy exposure to determine the noise exposure time remaining indicative of time remaining to achieve a threshold exposure level based on the received sound signal and the time signal; and
   generating, by the processor, an output signal indicative of a time remaining estimate.

15. The method of claim 14, wherein the instantaneous sound energy is calculated based on data from look up tables or pre-determined algorithms.

16. The method of claim 14, wherein the estimated future sound energy exposure is computed by extrapolation or pre-defined sound exposure history.

17. The method of claim 14, wherein the output signal indicative of the time remaining estimate is transmitted to an output device.

* * * * *